United States Patent
Prasad

(10) Patent No.: US 6,486,126 B1
(45) Date of Patent: *Nov. 26, 2002

(54) ANTIOXIDANT ACTIVITY IN SDG METABOLITES

(75) Inventor: Kailash Prasad, Saskatoon (CA)

(73) Assignee: University of Saskatchewan Technologies Incorporated, Saskatchewan (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/599,958

(22) Filed: Jun. 23, 2000

Related U.S. Application Data

(60) Provisional application No. 60/141,254, filed on Jun. 30, 1999.

(51) Int. Cl.[7] ............... A01N 43/04; C07H 15/24; A61K 31/74
(52) U.S. Cl. ............... 514/25; 514/885; 536/18.1; 424/78.08
(58) Field of Search ............... 514/25, 885; 536/18.1; 424/78.08

(56) References Cited

U.S. PATENT DOCUMENTS

| | | | |
|---|---|---|---|
| 5,837,256 A | 11/1998 | Clark et al. | 424/195.1 |
| 5,846,944 A | 12/1998 | Prasad | 514/25 |

OTHER PUBLICATIONS

Klosterman et al., "The Constitution of Linocinnamarin[1]", Contribution From the Department of Agricultural Chemistry, North Dakota Agricultural Experiment Station, and Department fo Agricultural Biochemistry, University of Minnesota, vol. 77, pp. 420 and 421, Jul. 29, 1954.

Klosterman et al., "The Glucosides of Flaxseed. II. Linocaffein[1]", Contribution From the Department of Agricultural Chemistry, North Dakota Agricultural College, vol. 81, pp. 2188–2191, Sep. 25, 1958.

Obermeyer eta l., "Chemical Studies of Phytoestrogens and Related Compounds in Dietary Supplements: Flax and Chaparral (43824)", pp. 6–12, 1995.

Bambagiotti–Alberti et al., "Revealing the Mammalian Lignan Precursor Seoisolariciresinol Diglucoside in Flax Seed by Ionspray Mass Spectrometry", Rapid Communications in Mass Spectrometry, vol. 8, pp. 595–598 (1994).

Harris et al., "Arrays for Potentially Anticarcinogenic Phytochemicals in Flaxseed", Cereal Foods World, vol. 38, No. 3, pp. 147–151, Mar. 1993.

MacRae et al., "Biological Activities of Lignans", Phytochemistry, vol. 23, No. 6, pp. 1207–1220, 1984.

Klosterman et al., "The Isolation of β–methylglutaric Acid from the seed of Flax", Contribution from the Department of Agricultural Chemistry, North Dakota Agricultural Experiment Station, adn Department of Argricultural Biochemistry, University of Minnesota, vol. 76, pp. 1229 and 1230, Mar. 5, 1954.

Primary Examiner—Jezia Riley

(57) ABSTRACT

The compounds secoisolariciresinol (SECO), enterodiol (ED) and enterolactone (EL), which are metabolites of secoisolariciresinol diglucoside obtained from flaxseed, are used for the treatment of diseases or conditions requiring administration of an antioxidant. Diseases or conditions that may be treated include hypercholesterolemic atherosclerosis, type I and type II diabetes, ischemic heart disease, heart failure, endotoxic and hemmorhagic shock, inflammatory bowel disease, rheumatoid arthritis, Parkinson's disease, and stroke.

4 Claims, 5 Drawing Sheets

*P<0.05, BL vs others
†P<0.05, BL + zym vs others
ᵃP<0.05, SDG vs SECO, ED, EL or α-TP
ᵇP<0.05, SECO vs ED, EL or α-TP
ᶜP<0.05, ED vs EL or α-TP
ᵈP<0.05, EL vs α-TP

500
ANTIOXIDANT ACTIVITY IN SDG METABOLITES

CROSS-REFERENCE TO RELATED APPLICATION

This application claims the benefit of U.S. Provisional Application No. 60/141,254, filed Jun. 30, 1999.

BACKGROUND OF THE INVENTION

This invention relates to a method for the use of metabolites of secoisolariciresinol diglucoside (SDG) for the treatment of diseases or conditions requiring administration of an antioxidant. These metabolites include secoisolariciresinol (SECO), enterodiol (ED) and enterolactone (EL).

Reactive oxygen species, which include superoxide anion ($O_2^-$), hydrogen peroxide ($H_2O_2$), hydroxyl radical (.OH) and singlet oxygen ($^1O_2$), have been implicated in the pathophysiology of numerous diseases, including hypercholesterolemic atherosclerosis, diabetes mellitus, ischemic/reperfusion injury, volume or pressure overload heart failure, hemorrhagic shock, endotoxic shock, ageing, inflammatory bowel disease (Crohn's disease, ulcerative colitis), Parkinson's disease, rheumatoid arthritis and stroke.

Antioxidants such as vitamin E, secoisolariciresinol diglucoside (SDG), probucol, vitamin C, superoxide dismutase, catalase, sulphasalazine, and various other drugs without antioxidant activity, have been shown to be effective to a varying degree in the diseases referred to above. These drugs, with the exception of vitamin C and E and SDG, are expensive and have adverse side effects.

As described in Prasad, U.S. Pat. No. 5,846,944, incorporated herein by reference, SDG, isolated from flaxseed, has been shown to be effective in lowering cholesterol, and in reducing the development of atherosclerosis in hypercholesterolemic rabbits. It is also effective in reducing the incidence of diabetes mellitus and preventing endotoxic shock.

SUMMARY OF THE INVENTION

Reactive oxygen species are known to be involved in the pathophysiology of ageing and numerous diseases, such as hypercholesterolemic atherosclerosis, type I and type II diabetes, ischemic heart disease, heart failure, endotoxic and hemmorhagic shock, inflammatory bowel disease, rheumatoid arthritis, Parkinson's disease, and stroke.

Secoisolariciresinol diglucoside (SDG), which is obtained from flaxseed, is metabolized to secoisolariciresinol (SECO), enterodiol (ED), and enterolactone (EL). A description of the above metabolites can be found in a report by R. K. Harris et al. (1991) Methods Development for Phytochemical Compliance Markers in Designer Foods (Flaxseed Powder), Midwest Research Institute. These metabolites are respectively 4.86, 5.02, and 4.35 times more potent than vitamin E, and 3.82, 3.95, and 3.43 times more potent than SDG. Vitamin E, SDG and various other drugs, some with antioxidant activity and some without, are currently used for the treatment of the above diseases.

Drugs presently used to treat the diseases listed above, are expensive and have been less than satisfactory for the treatment of these diseases because of their adverse side effects. The discovery of SDG metabolites offers a safe, less expensive antioxidant that is useful in the treatment of these diseases and conditions. They are derived from dietary flaxseed and are therefore from a natural source, having little to no side effects.

Thus, the present invention relates to the use of secoisolariciresinol (SECO), enterodiol (ED) or enterolactone (EL) for the treatment of diseases or conditions requiring administration of an antioxidant. These diseases or conditions include hypercholesterolemic atherosclerosis, type I and type II diabetes, ischemic heart disease, heart failure, endotoxic and hemmorhagic shock, inflammatory bowel disease, rheumatoid arthritis, Parkinson's disease, and stroke.

The SECO, ED or EL is preferably used in purified form and can be administered orally or intravenously. It can, for instance, be administered in a once daily oral dosage of about 5–15 mg per kg of body weight. The oral doses may conveniently be in the form of tablets or capsules and these metabolites may be used together with a variety of pharmaceutically acceptable diluents or carriers.

Morbidity and mortality associated with the diseases referred to above and their complications, such as lost wages, increased health costs and social burdens, are enormous. Treatment with the metabolites according to this invention serve to reduce or prevent the late complications associated with these diseases. The morbidity and mortality associated with these diseases is reduced or prevented. This reduces the burden of illness to society, and overall health care costs, and permit these patients to return to the workplace and be productive members of society.

DESCRIPTION OF THE PREFERRED EMBODIMENTS

Measurement of Antioxidant Activity

Figure 4:
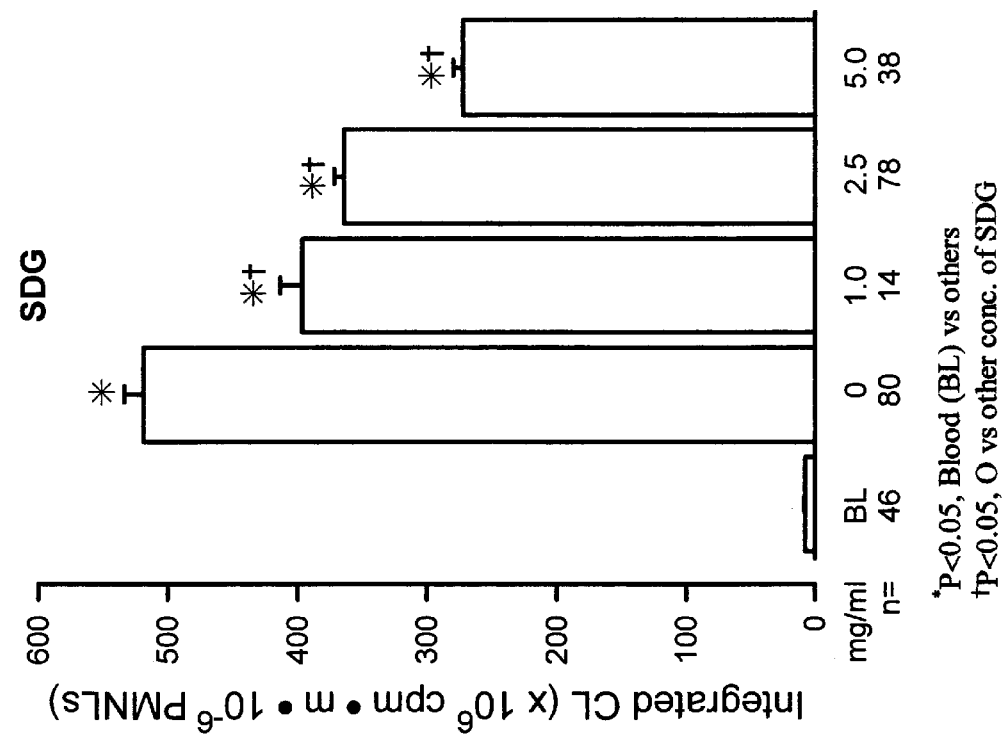
FIG. 4 is a bar graph showing the effects of various concentrations of SDG on zymosan-stimulated PMNL-CL.

Antioxidant activity of SDG, SECO, ED, EL and vitamin E (alpha-tochopherol phosphate) was measured using the ability of these compounds to reduce the chemiluminescence of activated PMNLs [polymorphonuclear leukocytes chemiluminescence (PMNL-CL)]. Activated polymorphonuclear leukocytes produce superoxide anion ($O_2^-$), hydrogen peroxide ($H_2O_2$), hydroxyl radical (.OH) and singlet oxygen ($^1O_2$). Chemiluminescence is amplified by luminol, which is converted to an excited aminophthalate ion in the presence of oxidizing species like $O_2^-$, $H_2O_2$, .OH and $^1O_2$. Luminol-dependent CL reflects the amount of activated oxygen species generated from activated phagocytes, thus, this method can be used to monitor the reactive oxygen species produced by PMNLs. Agents which scavenge $O_2^-$, $H_2O_2$, .OH and $^1O_2$ would reduce PMNL-CL. The SDG, SECO, ED and EL were all obtained from Agriculture and Agri-Food Canada, Saskatoon, Saskatchewan.

Venous blood from healthy subjects, after their informed consent, was collected in ethylenediamine tetraacetic acid (EDTA)-containing tubes for PMNL counts, and PMNL-CL. PMNL and WBC counts were made using Technicon H6000 system (Technicon Instruments, Tarrytown, N.Y.). PMNL-CL a measure of reactive oxygen species produced by PMNLs was measured by a method described in Prasad et al., Effect of polymorphonuclear leukocyte-derived oxygen free radicals and hypochlorous acid or cardiac function and some biochemical parameters, Am. Heart J. 119:538–550, 1990. Blood (0.05 ml) was added to a glass tube containing Hank's balanced salt solution (HBSS) buffer (pH 7.40) and luminol at a final concentration of $10^{-4}$ M. To assess the ability of various test materials in the varying amounts (1.0, 2.5, 5.0 and 10 mg/ml) in the powder form, were each added to the test tube containing blood, shaken well and incubated for 15 minutes at room temperature. The final volume of the mixture in these tubes was 0.5 ml. All the test tubes were placed in a luminometer for 5 min at 37° C., and phagocytosis was initiated by the addition of 0.1 ml (10 mg/ml) of opsonized zymosan prepared by previously described method (Prasad et al., 1990). The chemiluminescence was monitored with an Auto Lumat, LB953 luminometer (Egg Berthold, Berthold Analytical Instrument Inc., 472 Amherst Street, Nashua, N.H., 03063) for 3 seconds every 2 or 3 minutes (depending on the sample number) for a period of 60 minutes. The integrated area under the curve gives the total luminal-dependent chemiluminescent response during the period of monitoring, which represents the oxygen derived CL. The difference in the integrated area under zymosan-activated in the absence and in the presence of various compounds under investigation is designated as particular compound inhibitable oxygen derived radical CL. The unit for chemiluminescence is in counts per minute (cpm). The integrated area under the curve is in cpm.m. The unit for chemiluminescence is cpm.m.$10^{-6}$ PMNLs because the chemiluminescence is expressed in terms of $10^{-6}$ PMNL counts. The peak chemiluminescence is cpm $10^{-6}$ PMNLs.

Statistical Analysis

The results are expressed as mean±SE and n=sample size. One-way Analysis of Variance (ANOVA) followed by Scheffe test was used to derive differences between different groups. A "p" value of less than 0.05 was considered significant.

Comparison of the Antioxidant Activity

Figure 1:
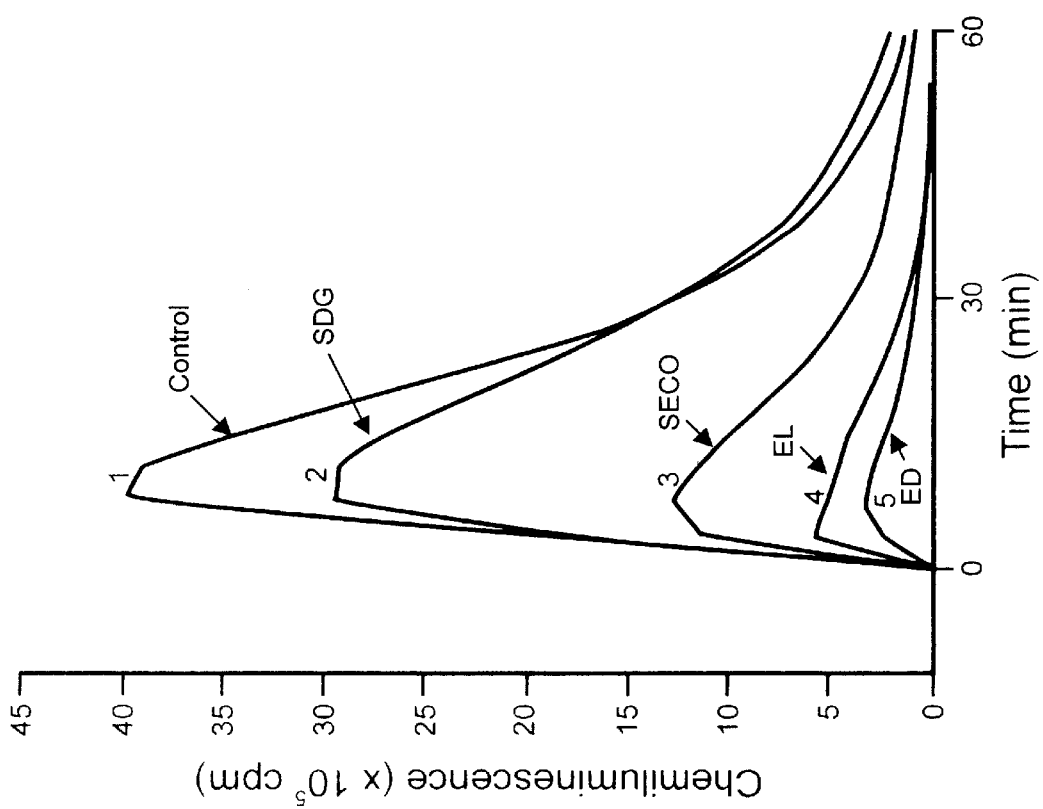
FIG. 1 is representative tracings showing changes in the chemiluminescence (CL) of zymosan-stimulated polymorphonuclear leukocytes chemiluminescence (PMNL-CL) in the (1) absence of and in the presence of 2.5 mg/ml of SDG (2), SECO (3), EL (4) or ED (5).
Figure 2:
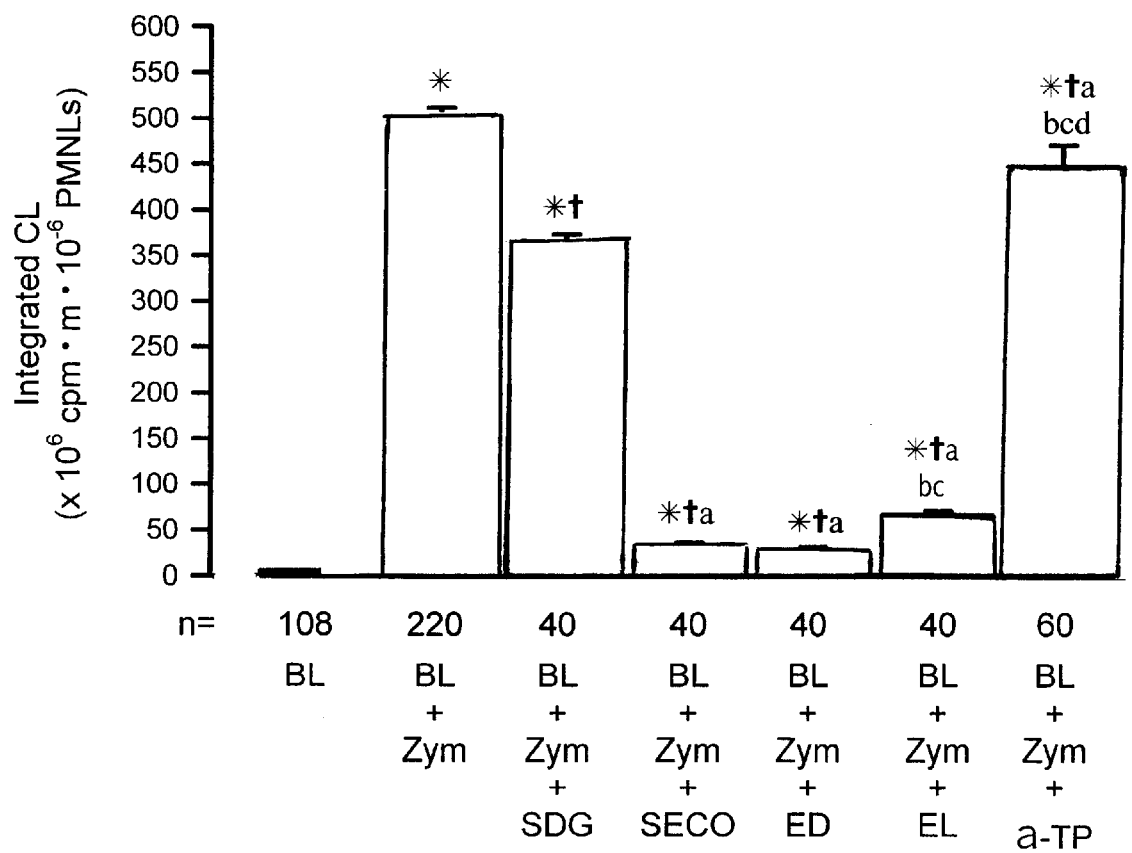
FIG. 2 is a bar graph showing changes in the integrated CL of unstimulated blood (BL) or zymosan-stimulated blood in the absence of or in the presence of SDG, SECO, ED, EL or Vitamin E [α-tochopherol (α-TP)], each in a concentration of 2.5 mg/ml.
Figure 3:
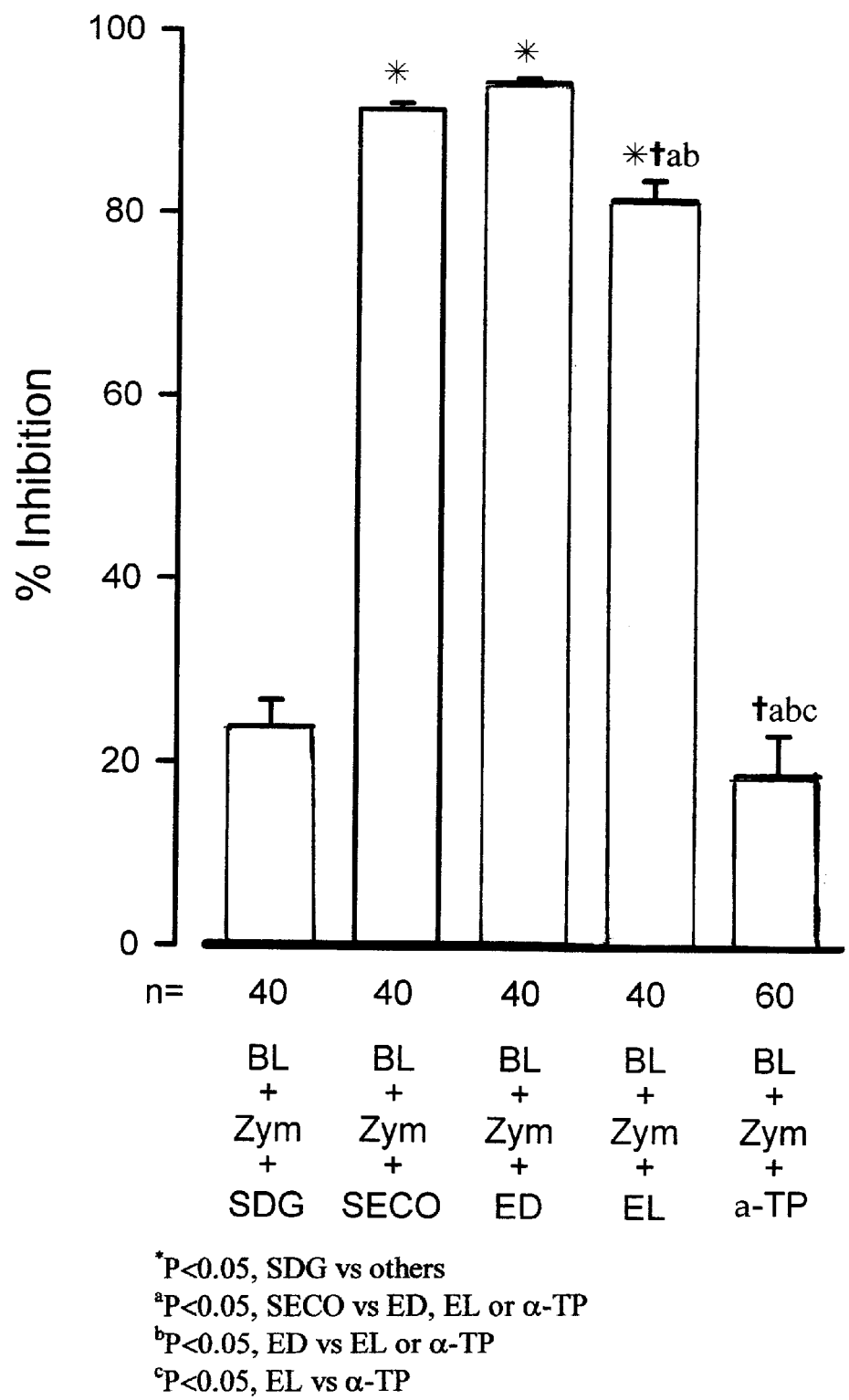
FIG. 3 is a bar graph showing the percent inhibition of PMNL-CL by SDG, SECO, ED, EL and α-TP in similar concentration (2.5 mg/ml).

A typical tracing of the chemiluminescence (CL) of zymosan-activated PMNLs in blood in the absence or presence of SDG, SECO, EL or ED is shown in FIG. 1. The chemiluminescent activity of PMNLs increased rapidly with the addition of zymosan and reached a peak value within 8–10 min. After its peak, it decreased slowly for the duration of the observation period to reach at prestimulated value at the end of 60 min. SDG, SECO, EL, ED and vitamin E each in the concentration of 2.5 mg/ml decreased chemiluminescent activity of zymosan stimulated PMNLs to varying degrees. The results of the effects of SDG, SECO, EL, ED and vitamin E on the integrated-CL of unstimulated- or zymosan-stimulated blood are summarized in Table I and FIG. 2. There was an increase of approximately 85 folds in the integrated CL with zymosan in the untreated blood. SDG, SECO, EL and ED produced a reduction in CL by 39%, 76%, 48% and 73% respectively in the unstimulated blood (Table I). The percentage inhibition of PMNL-CL with SDG, SECO, ED, EL and vitamin E (α-TP) are shown in FIG. 3. SDG and vitamin E in the concentration of 2.5 mg/ml produced inhibition to similar extent (23.87% vs. 18.75%). SECO and ED produced similar inhibition (91.2% vs. 94.22%). The inhibition produced by EL was 81.57%. The antioxidant activity was highest with SECO and ED and lowest with SDG and vitamin E. The order of antioxidant potency was SECO=ED>EL>SDG=vit. E. The antioxidant potency of SECO, ED, EL and SDG was 4.86, 5.02, 4.35, 1.27 respectively as compared to vitamin E.

TABLE 1

Integrated CL (×$10^6$ cpm · m · $10^{-6}$ PMNLs) of unstimulated blood (BL) in the absence and presence of SDG, SECO, EL or ED

| BL | BL + SDG |
|---|---|
| 4.038 ± 0.143 | 2.463 ± 0.159* |
|  | (39) |
| BL | BL + SECO |
| 3.654 ± 0.346 | 0.878 ± 0.023* |
|  | (76) |
| BL | BL + EL |
| 4.168 ± 0.499 | 2.177 ± 0.138* |
|  | (48) |
| BL | B + ED |
| 4.038 ± 0.143 | 1.073 ± 0.048* |
|  | (73) |

The results are expressed as mean ± SE from 16 samples each. BL, blood; SDG, secoisolariciresinol diglucoside; SECO, secoisolariciresinol; EL, enterolactone; ED, enterodiol. The numbers in the bracket show the percent reduction of CL by the particular compound.
*P < 0.05, BL vs. BL + SDG, BL + SECO, BL + EL, or BL + ED.

Concentration-dependent Response

The effects of 1.0, 2.5, 5.0 and 10.0 mg/ml of SDG, SECO, ED, EL and vitamin E on the zymosan-stimulated PMNL-CL were investigated to determine if the antioxidant activity was concentration-dependent. Effects of various concentrations of SDG on zymosan-stimulated PMNL-CL are shown in FIG. 4. Zymosan in the absence of SDG produced a marked increase in the PMNL-CL. SDG produced a concentration-dependent inhibition of PMNL-CL, the inhibition being 24% with 1.0 mg/ml, 30% with 2.5 mg/ml and 48% with 5.0 mg/ml.

Figure 5:
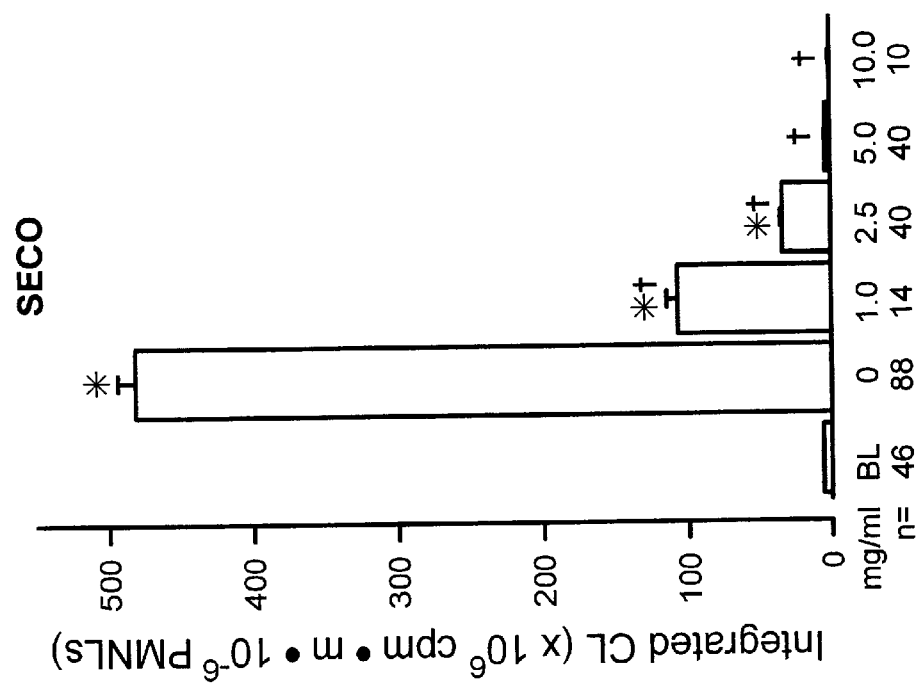
FIG. 5 is a bar graph showing the effects of various concentrations of SECO on zymosan-stimulated PMNL-CL.

Effects of various concentrations of SECO are summarized in FIG. 5. Zymosan in the absence of SECO produced a marked increase in the PMNL-CL. SECO in the concentration of 1.0, 2.5, 5.0 and 10.0 mg/ml produced an inhibition of zymosan-stimulated PMNL-CL by 78%, 93%, 99.5% and 100% respectively. It appears that 5.0 mg/ml almost completely inhibited the PMNL-CL.

Figure 6:
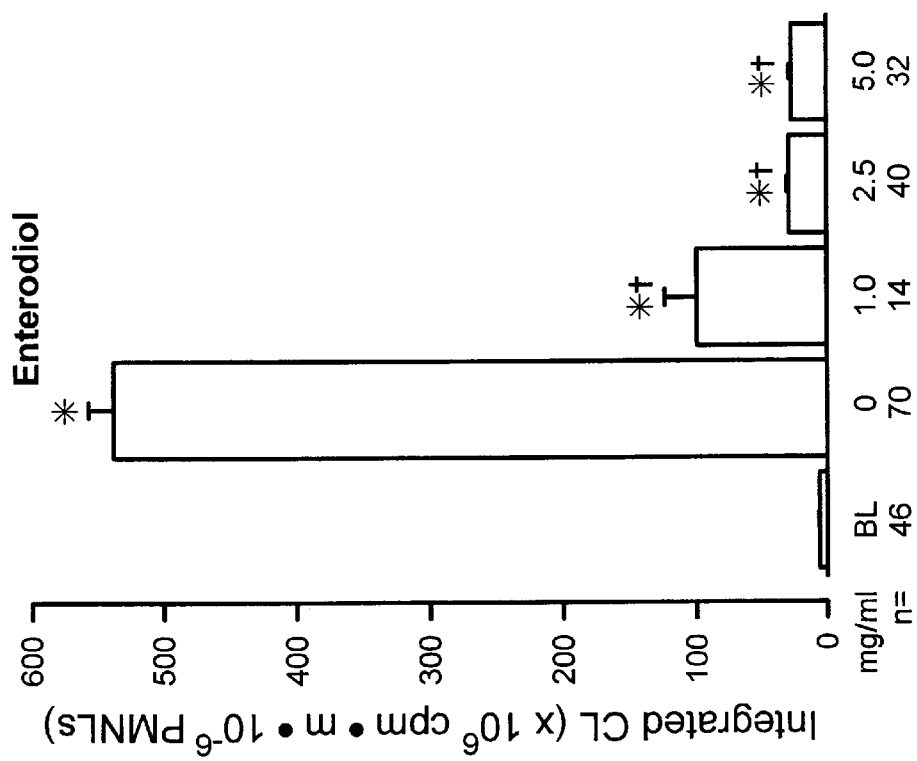
FIG. 6 is a bar graph showing the effects of various concentrations of ED on zymosan-stimulated PMNL-CL.

Effects of various concentrations of ED on zymosan-stimulated PMNL-CL are shown in FIG. 6. Zymosan in the absence of ED produced a significant increase in the PMNL-CL. ED inhibited the PMNL-CL by 82%, 96% and 95% respectively in the concentration of 1.0, 2.5 and 5.0 mg/ml. The concentration of 2.5 and 5.0 mg/ml has similar effects.

Figure 7:
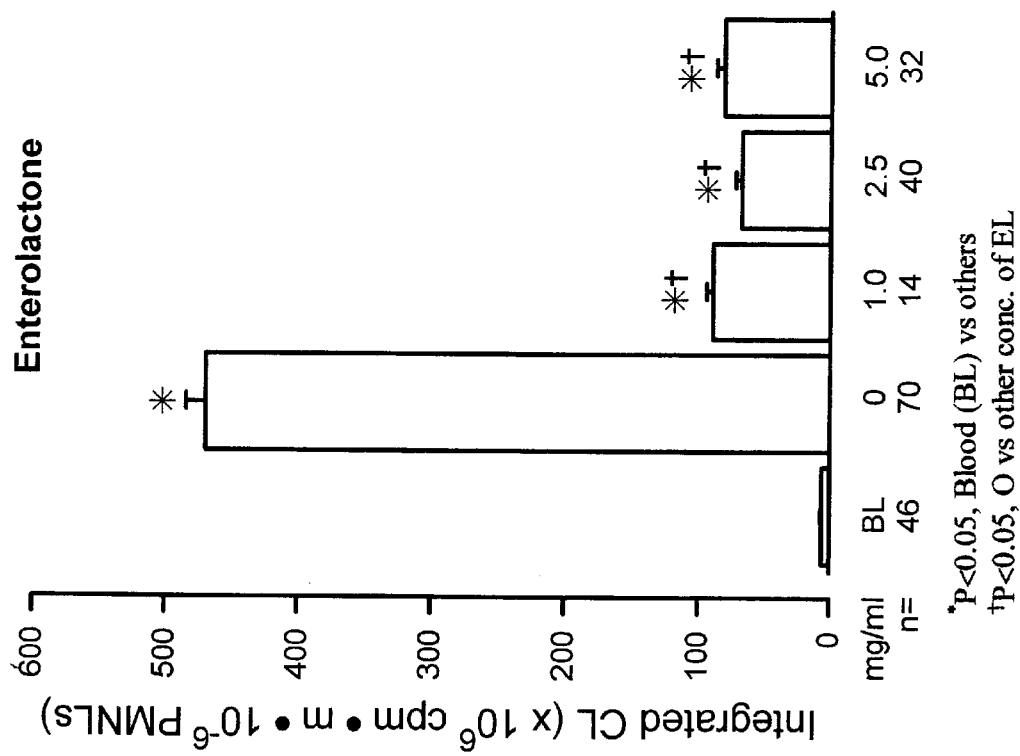
FIG. 7 is a bar graph showing the effects of various concentrations of EL on zymosan-stimulated PMNL-CL.

Effects of various concentrations of EL on the zymosan-stimulated PMNL-CL are summarized in FIG. 7. In the concentration of 1.0, 2.5 and 5.0 mg/ml, it produced an inhibition of PMNL-CL by 81%, 86% and 83% respectively. It appears that maximum effect is obtained with 1.0 mg/ml of EL.

Figure 8:
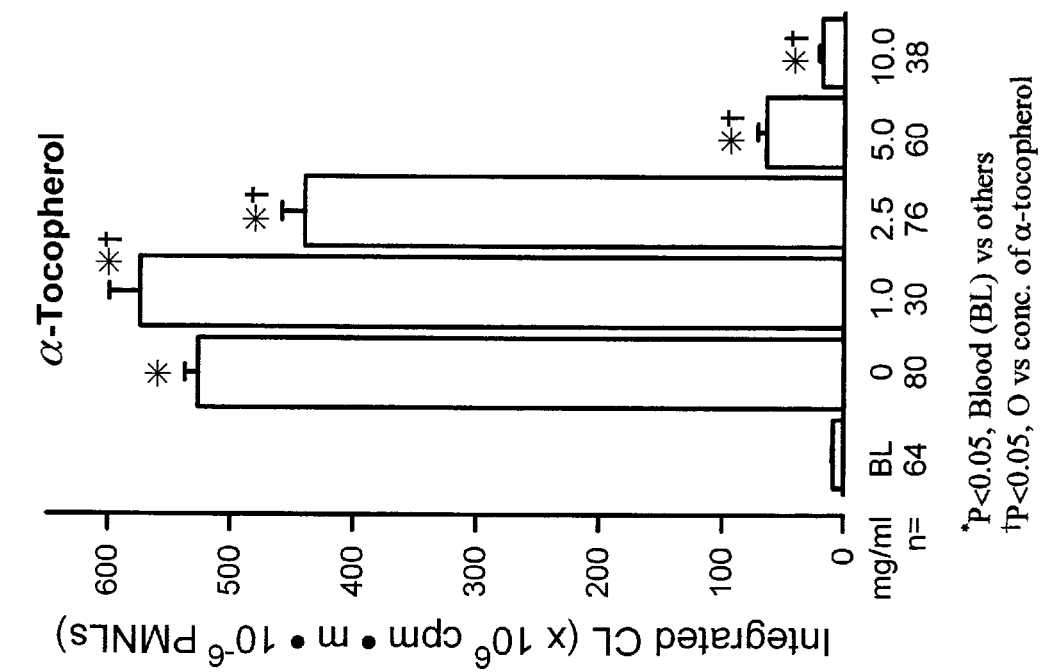
FIG. 8 is a bar graph showing the effects of various concentrations of α-TP on zymosan-stimulated PMNL-CL.

Effects of various concentrations of α-tochopherol (α-TP) on the zymosan-stimulated PMNL-CL are shown in FIG. 8. In the concentration of 1.0 mg/ml, it produced an increase in the PMNL-CL. However in the concentrations of 2.5, 5.0 and 10.0 mg/ml it produced an inhibition of 17%, 88% and 97% respectively. It appears that in small concentrations it stimulates PMNLs.

These results indicate that SDG, SECO, ED, and EL are scavengers of $O_2^-$, $H_2O_2$, .OH and $^1O_2$ and are therefore antioxidants.

REFERENCES

Allen, R. C., and L. D. Loose. Phagocytic activation of luminol-dependent chemiluminescence in rabbit alveolar and peritoneal macrophages. Biochem. Biophys. Res. Commun. 69: 245–252, 1976.

Anthonisen, P., F. Barany, O. Folkenborg et al. The clinical effect of salazosulphapyridine (Salazopyrin) in Crohn's disease. A controlled double-blinded study. Scand. J. Gastroent. 9: 549–554, 1974.

Babior, B. M. The respiratory burst of phagocytes. J. Clin. Invest. 73: 599–601, 1984.

Dick, A. P., M. J. Grayson, R. G. Carpenter, and A. Petrie. Controlled trial of sulphasatazine in the treatment of ulcerative colitis. Gut 5: 437–442, 1964.

Emerit, J., S. Pelletier, D. Tosoni-Verilgnue, M. Mollet. Phase II trial of copper zinc superoxide dismutase (CuZn SOD) in the treatment of Crohn's disease. Free Radic. Biol. Med. 7: 145–149, 1989.

Fantone, J. C., and P. A. Ward. Role of oxygen derived free radicals and metabolites in leukocyte-dependent inflammatory reactions. Am. J. Pathol. 107: 397–418, 1982

Halliwell, B., J. M. C. Guttenridge, E. Cross. Free radicals, antioxidants and human disease: Where are we now? J. Lab. Clin. Med. 119: 598–620, 1992.

Jain, S. K., S. N. Levine, J. Duett, and B. Hollier. Elevated lipid peroxidation levels in red blood cells of streptozotoxin- treated diabetic rats. Metabolism. 39: 971–975, 1990.

Kakkar, R., J. Kalra, S. V. Mantha, and K. Prasad. Lipid peroxidation and activity of antioxidant enzymes in diabetic rats. Mol. Cell. Biochem. 151: 113–119, 1995.

Kakkar, R., S. V. Mantha, J. Radhi, K. Prasad, and J. Kalra. Increased oxidative stress in rat liver and pancreas during progression of streptozotoxin-induced diabetes. Clin. Sci. 94: 623–632, 1998.

Kalra, J. A. H. Rajput, S. V. Mantha, A. K. Chaudhary, and K. Prasad. Oxygen free radical producing activity of polymorphonuclear leukocyte in patients with Parkinson's disease. Mol. Cell. Biochem. 112: 181–186, 1992.

Kapoor, R., and K. Prasad. Role of oxyradicals in cardiovascular depression and cellular injury in hemorrhagic shock and reinfusion: Effect of SOD and catalase. Circ. Shock 43: 79–94, 1994.

Kapoor, R., and K. Prasad. Role of polymorphonuclear leukocytes in cardiovascular depression and cellular injury in hemorrhagic shock and reinfusion. Free Radic. Biol. Med. 21:609–618, 1996.

McCord, J. M. Free radicals and inflammation protection of synorial fluid by superoxide dismutase. Science 185: 529–531, 1974.

Pattanaik, U., and K. Prasad. Endotoxemia and oxidative stress. Ann. NY Acad. Sci. 793: 506–510, 1996.

Pattanaik, U., and K. Prasad. Oxygen free radicals and endotoxic shock: Effect of flaxseed. J. Cardiovasc. Pharmacol. Therapeut. 3: 305–318, 1998.

Peppercorn, M. A. Advances in drug therapy for inflammatory bowel disease. Ann. Modern Med. 112: 50–60, 1990.

Prasad, K. Hydroxyl radical-scavenging property of secoisolariciresinol diglucoside (SDG) isolated from flaxseed. Mol. Cell. Biochem. 168: 117–123, 1997.

Prasad, K. Use of purified SDG as an antioxidant. U.S. Pat. No. 5,846,944, Dec. 8, 1998a.

Prasad, K. Prevention of IDDM in BBdp rats by secoisolariciresinol diglucoside (SDG) isolated from flaxseed. Diabetes 47(Suppl I): A360, 1998b.

Prasad, K. Reduction of serum cholesterol and hypercholesterolemic atherosclerosis in rabbits by secoisolariciresinol diglucoside (SDG) isolated from flaxseed. Circulation 99: 1355–1362, 1999.

Prasad, K., A. K. Chaudhary, and J. Kalra. Oxygen-derived free radical producing activity and survival of activated polymorphonuclear leukocytes. Mol. Cell. Biochem. 103: 51–62, 1991.

Prasad, K., D. Debnath, J. Kalra, P. Lee. Effects of dimethylthiourea on the cardiac function and oxyradical status in ischemia-reperfusion injury. Ann. NY Acad. Sci. 723: 375–379, 1994a.

Prasad, K., J. B. Gupta, J. Kalra, P. Lee, S. V. Mantha and B. Bharadwaj. Oxidative stress as a mechanism of cardiac failure in canine model. J. Mol. Cell. Cardiol. 28: 375–385, 1996.

Prasad, K., and J. Kalra. Oxygen free radicals and hypercholesterolemic atherosclerosis: Effect of vitamin E. Am. Heart J. 125: 958–973, 1993.

Prasad, K., J. Kalra, J., B. Bharadwaj, A. K. Chaudhary. Increased oxygen free radical activity in patients on cardiopulmonary bypass undergoing aorta-coronary bypass surgery. Am. Heart. J. 123: 37–45, 1992.

Prasad, K., J. Kalra, A. K. Chaudhary, and D. Debnath. Effect of polymorphonuclear leukocyte-derived oxygen free radicals and hypochlorous acid on cardiac function and some biochemical parameters. Am. Heart. J. 119: 538–550, 1990.

Prasad, K., J. Kalra, and P. Lee. Oxygen free radicals as a mechanism of hypercholesterolemic atherosclerosis: Effects of probucol. Int. J. Angiol. 3: 100–112, 1994b.

Prasad, K., S. V. Mantha, J. Kalra, R. Kapoor, and B. R. C. Kamalarajan. Purpurogallin in the retardation of hypercholesterolemic atherosclerosis. Intl. J. Angiol. 6: 157–166, 1997a.

Prasad, K., S. V. Mantha, J. Kalra, and P. Lee. Prevention of hypercholesterolemic atherosclerosis by garlic, an antioxidant. J. Cardiovasc. Pharmacol. Therapeut. 2: 309–320, 1997b.

Rickard, S. E., L. J. Orcheson, M. M. Seidl, L. Luyengi, H. H. S. Fong, and L. U. Thompson. Dose-dependent production of mammalian lignans in rats and in vitro from the purified precursor secoisolariciresinol diglucoside in flaxseed. J. Nutr. 126: 2012–2019, 1996.

Pickard, S. E., and L. U. Thompson. Chronic exposure to secoisolariciresinol diglucoside alters lignan disposition in rats. J. Nutr. 128: 615–623, 1998.

Simpson, P. J., and B. R. Lucchesi. Free radicals and myocardial ischemia and reperfusion injury. J. Lab. Clin. Med. 110: 13–30, 1987.

Steinberg, D. Antioxidants in the prevention of human atherosclerosis. Circulation 85: 2338–2345, 1992.

Stevens, P., D. J. Winston, and K. Van Dyke. In vitro evaluation of opsonic and cellular granulocyte function by luminol-dependent chemiluminescence: Utility in patients with severe neutropenia and cellular deficiency states. Infect. Immunity 22: 41–51, 1978.

Yu, B. P. Free radicals in ageing. C.R.C. Press, Boca Raton, 1993.

The disclosures of the above articles are specifically incorporated herein by reference.

What is claimed is:

1. A method of treatment of a disease or a condition selected from the group consisting of hypercholesterolemic atherosclerosis and diabetes type I or type II, which comprises administering to a patient an effective amount of a secoisolariciresinol diglucoside (SDG) metabolite selected from the group consisting of secoisolariciresinol (SECO) enterodiol (ED) and enterolactone (EL).

2. A method according to claim 1, wherein the metabolites are used at a purity of at least 90%.

3. A method of treatment of hypercholesterolemic atherosclerosis which comprises administering to a patient an effective amount of a secoisolariciresinol diglucoside (SDG) metabolite selected from the group consisting of secoisolariciresinol (SECO) enterodiol (ED) and enterolactone (EL) at a purity of at least 90%.

4. A method of treatment of diabetes type I or type II, which comprises administering to a patient an effective amount of a secoisolariciresinol diglucoside (SDG) metabolite selected from the group consisting of secoisolariciresinol (SECO) enterodiol (ED) and enterolactone (EL) at a purity of at least 90%.

* * * * *